(12) United States Patent
Dickie

(10) Patent No.: US 6,536,066 B2
(45) Date of Patent: Mar. 25, 2003

(54) TOOTHBRUSH OSCILLATING HEAD

(75) Inventor: Robert G. Dickie, Newmarket (CA)

(73) Assignee: Pulse Innovations Inc., Toronto (CA)

( * ) Notice: Subject to any disclaimer, the term of this patent is extended or adjusted under 35 U.S.C. 154(b) by 0 days.

(21) Appl. No.: 09/911,413

(22) Filed: Jul. 25, 2001

(65) Prior Publication Data

US 2003/0019057 A1 Jan. 30, 2003

(51) Int. Cl.[7] .......................... A46B 7/08; A61C 17/16; A61C 17/34; A47L 13/02
(52) U.S. Cl. ............................... 15/22.1; 15/28
(58) Field of Search .............................. 15/22.1, 28, 29

(56) References Cited

U.S. PATENT DOCUMENTS

| | | | |
|---|---|---|---|
| 2,379,049 A | 6/1945 | Tompkins | |
| 4,479,516 A | 10/1984 | Hunter | |
| 4,989,287 A | 2/1991 | Scherer | |
| 5,353,460 A | * 10/1994 | Bauman | |
| 5,416,942 A | 5/1995 | Baldacci et al. | |
| 5,577,285 A | * 11/1996 | Drossler | |
| 5,617,603 A | * 4/1997 | Mei | |
| 5,625,916 A | 5/1997 | McDougall | |
| 5,784,743 A | 7/1998 | Shek | |

* cited by examiner

*Primary Examiner*—Terrence R. Till
(74) *Attorney, Agent, or Firm*—Blake, Cassels & Graydon LLP; Terry L. Leier

(57) ABSTRACT

Discloses a bristle head oscillation mechanism for an electrically driven toothbrush. A toothbrush bristle head is rotatably disposed at an end of an elongate housing. A drive shaft is rotatably disposed in the elongate housing and has an offset end coupled to one end of a pivot arm. The other end of the pivot arm is coupled to the toothbrush bristle head. Rotation of the drive shaft pivots the pivot arm to effect oscillation of the bristle head with respect to the elongate housing.

24 Claims, 4 Drawing Sheets

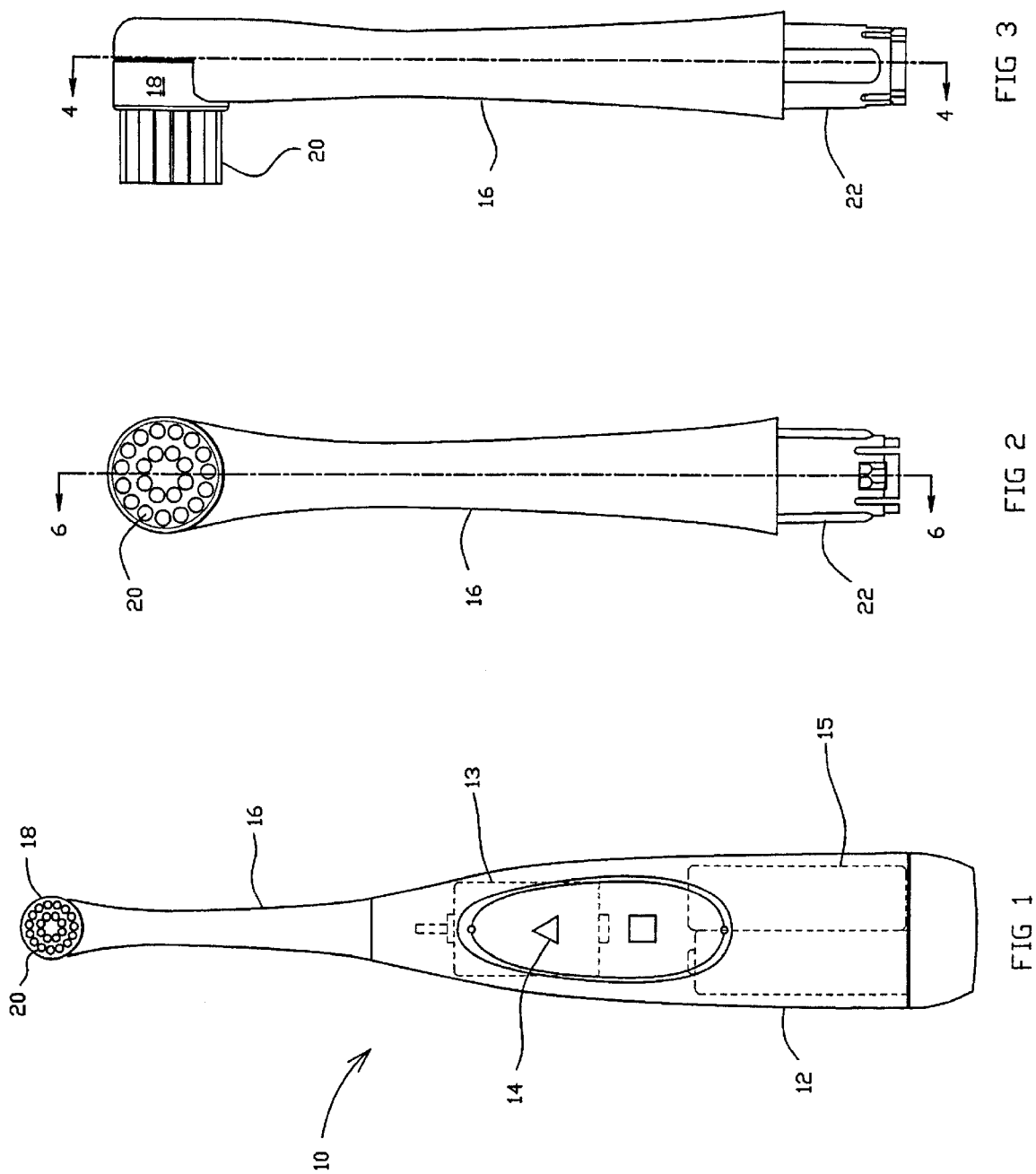

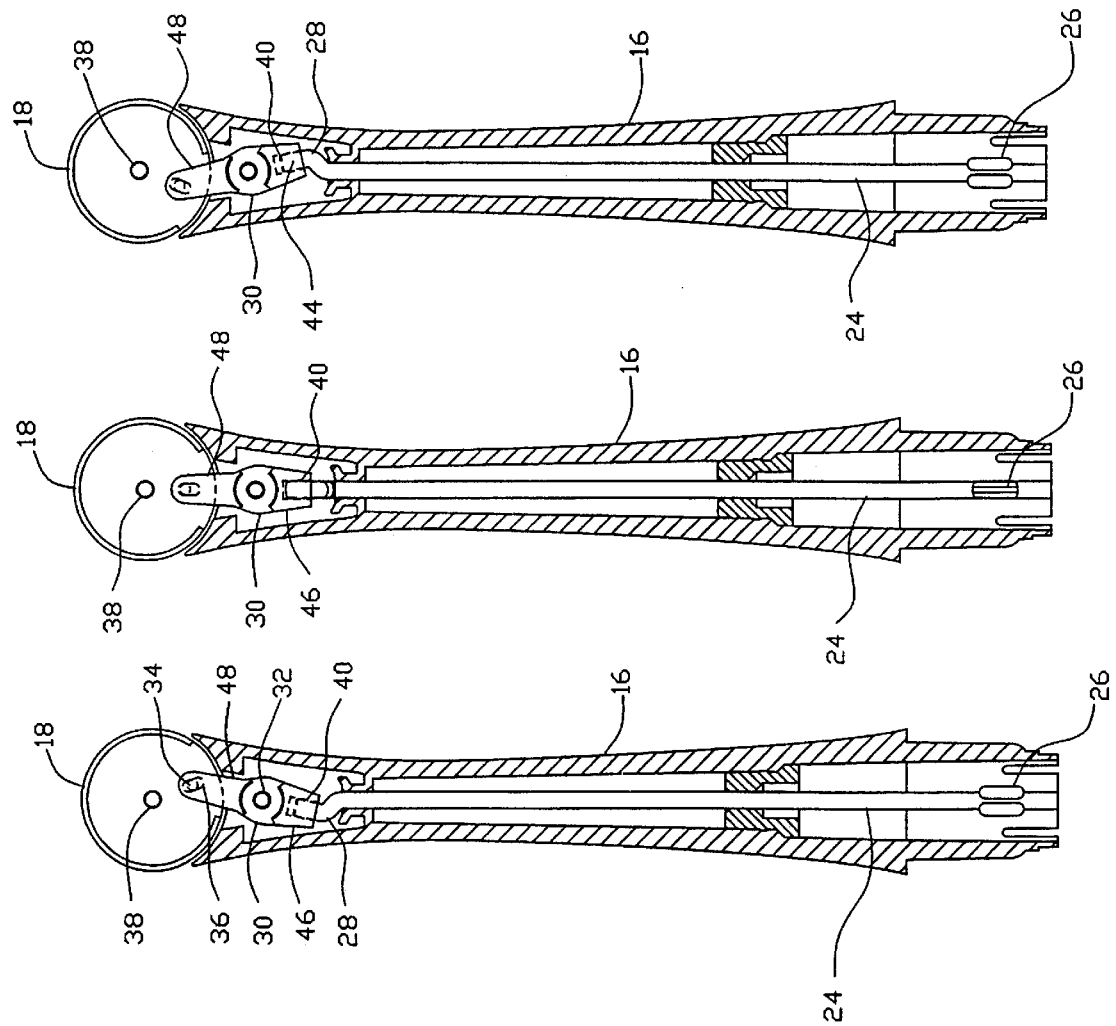

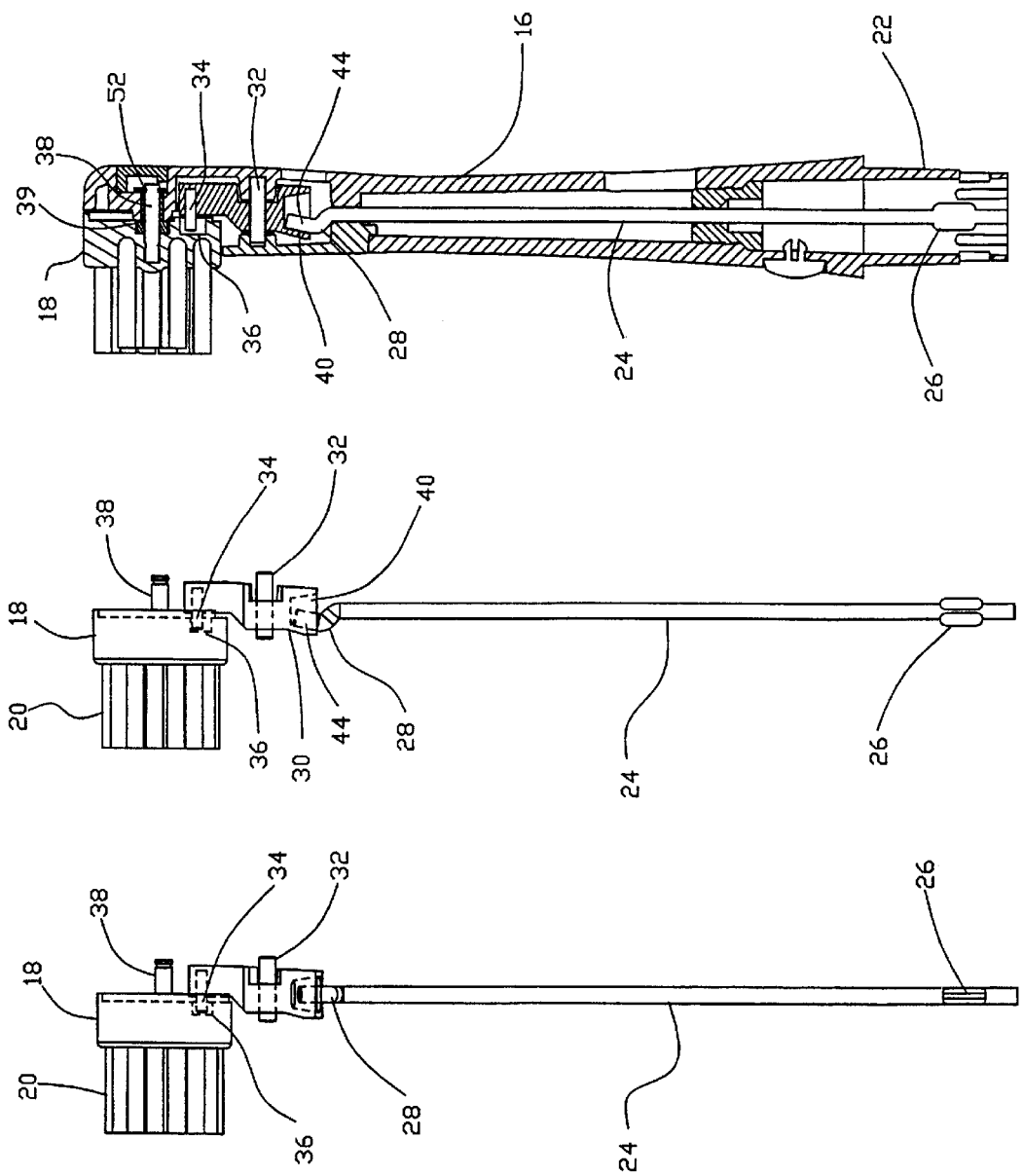

TOOTHBRUSH OSCILLATING HEAD

FIELD OF THE INVENTION

This invention relates to electrically operated toothbrushes and more particularly to an oscillating head mechanism for an electrically operated toothbrush.

BACKGROUND OF THE INVENTION

Electrically operated toothbrushes provide a device for cleaning teeth that has a mechanized bristle head which is operable to effect motion between the bristle head and the handle of the toothbrush to provide a scrubbing action to the teeth to which the bristle head is applied. Electrically operated toothbrushes provide a range of motions between the bristle head and the toothbrush handle to augment the scrubbing action the bristle heads apply to the teeth which are to be cleaned by the toothbrush.

Electric toothbrushes provide an oscillating motion to the bristle head have been described in the prior art including, for example, in U.S. Pat. No. 5,625,916 to McDougall. The disclosure of McDougall describes an electrically driven toothbrush having an oscillating head that is operable by rotation of a rotating shaft coupled to the head which is driven by an electric motor. The mechanism of McDougall provides a limited range of oscillation to the bristle head. Because the bristles extending from the bristle head of a toothbrush are flexible, the motion or movement of the portion of the other end of the bristles in contact with the teeth of a user is reduced from the motion imparted to the bristles by the bristle head. To promote cleaning of the teeth of a user, it is desirable to have an efficacious relative motion or scrubbing contact of the toothbrush bristles to the teeth and gum tissues of the user. Because of bristle flexibility, a limited range of motion of a bristle head can result in bristle end immobilisation when the toothbrush bristles are applied to the teeth or gums of a user. Bristle end immobilisation in has the undesirable result of an inefficacious rocking motion of the toothbrush bristle ends relative to the tooth and oral surfaces that are sought to be cleaned.

It is desirable to provide a range of motion of a toothbrush bristle head of an electric toother brush that facilitates a brushing action to be applied by the toothbrush bristles when engaged with the teeth and oral surfaces to be cleaned.

It is an object of the present invention to provide an electrically operable toothbrush with an oscillating bristle head driven through an efficacious range of motion relative to the toothbrush handle.

In one of its aspects, the invention provides a bristle head oscillation mechanism for an electrically driven toothbrush comprising an elongate housing having a drive shaft rotatably mounted therein. A bristle head is rotatably disposed at an end of the elongate housing and coupled to a pivot arm pivotable about a pivot axis depending from the housing. Opposing ends of the pivot arm are coupled to the drive shaft and to the bristle head respectively. Rotation of the drive shaft pivots the pivot arm to effect oscillation of the bristle head with respect to the elongate housing.

The preferred embodiments of the invention will now be described with reference to the accompanying drawings in which the same reference numerals are used to describe like features of the invention throughout the various figures of the drawings.

BRIEF DESCRIPTION OF THE DRAWINGS

FIG. 1 is an elevation view of an electric toothbrush incorporating features of the invention.

FIG. 2 is a front elevation view of a bristle head assembly portion of an electric toothbrush incorporating features of the invention.

FIG. 3 is a side elevation of the bristle head assembly of FIG. 2.

FIGS. 4a, 4b and 4c are cross-sectional views of a preferred embodiment of the bristle head assembly taken along cutting line 4—4 of FIG. 3.

FIGS. 5a and 5b are side elevation views exemplifying rotation orientations of the drive elements of a preferred embodiment of the present invention.

FIG. 6 is a cross-sectional view of a preferred embodiment of the bristle head assembly of the present invention taken along cutting line 6—6 of FIG. 2.

DETAILED DESCRIPTION OF THE PREFERRED EMBODIMENT

Figure 7:
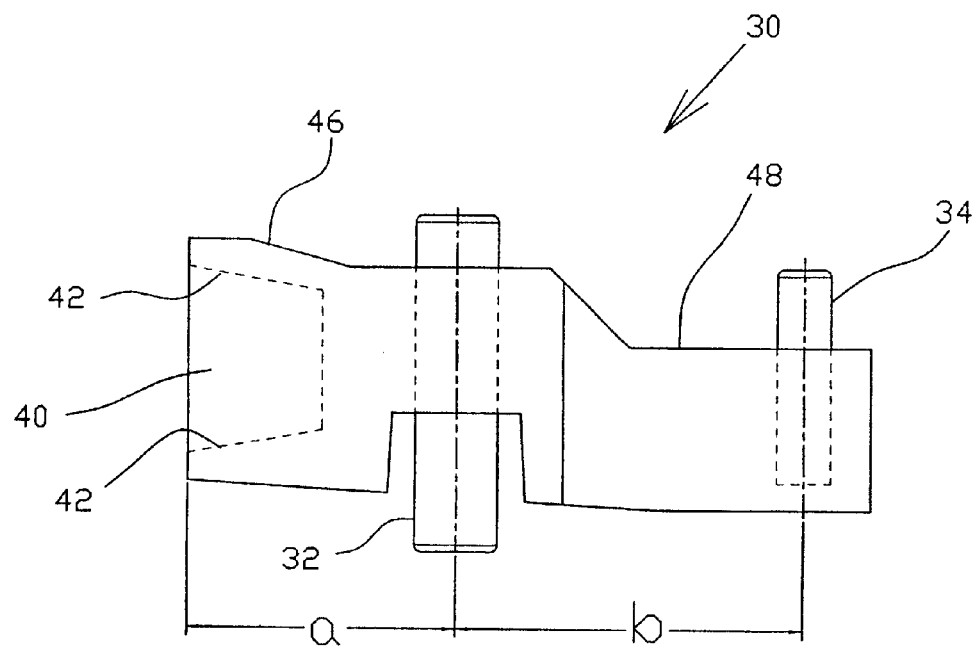
FIG. 7 is an enlarged view of a preferred embodiment of a preferred embodiment of a pivot lever.

FIG. 1 shows an elevation view of an electric toothbrush generally referenced by reference numeral 10. The electric toothbrush has a handle portion 12, which houses the toothbrush prime mover elements including an electric motor, shown in ghost outline form 13, and a power source, typically, a battery, shown in ghost outline form 15. The toothbrush 10 has a power switch 14 conveniently located on the device to control activation of the electric motor. The electric toothbrush includes a bristle head assembly 16 extending from an end of a handle portion 12 of the electric toothbrush. Generally, the bristle head assembly 16 is removably mountable on handle portion 12 of the electric toothbrush to facilitate replacement. The end of bristle assembly 16 remote from the handle portion 12 has a bristle head 18, which provides a mount for a plurality of bristle clusters 20 that the user applies to the teeth and oral surfaces to be cleaned.

FIG. 2 is a front elevation view of the bristle head assembly 16 which has a mount coupling 22 adapted to releasably engage the handle portion 12 of the electric toothbrush providing mechanical coupling between the bristle head assembly and the handle. When needed, for example, when bristles 20 become worn, a new bristle head assembly 16 can be mounted on the handle portion 12 to maintain optimal operation of the electric toothbrush. FIG. 3 is a side elevation view of the bristle head assembly 16 of FIG. 2.

FIGS. 4a, 4b and 4c are cross-section views of the backside of the bristle head assembly 16. Each respective FIG. 4a, 4b and 4c shows a different rotational position of drive shaft 24 and related drive apparatus to depict the rotating effect and consequent oscillating rotational displacement of the bristle head 18 in relation to the bristle head assembly 16. An end of drive shaft 24 includes an engagement coupling 26 that is adapted to mate with a rotating drive output of the prime mover in the handle 12 of the electric toothbrush 10 when the bristle head apparatus 16 is mounted thereon. In operation, drive shaft 24 is driven in rotation by the prime mover drive motor assembly and during the course of the rotation of drive shaft 24, it will rotate through the three orientations or positions shown in FIGS. 4a, 4b and 4c of the drawings. The end of drive shaft 24 remote from engagement coupling 26 is coupled to pivot arm 30. In the preferred embodiment, drive shaft 24 has an off set end 28 adapted to couple to a mating pivot drive slot 40 formed in an end of pivot arm 30. In operation, rotation of drive shaft 24, causes pivot arm 30 to rotate in an oscillatory motion about a pivot axis 32, depicted in the drawings of the preferred embodiment as an axle extending from pivot arm 30. In the position shown in FIG. 4a, the offset end 28 is rotated to a position corresponding to maximum clockwise rotation of pivot arm 30 about pivot axis 32. The end of pivot arm 30 remote from the offset 28 is coupled to the bristle head 1 8. In the preferred embodiment, coupling of the pivot arm 30 to bristle head 18 is effected by a drive pin 34 that engages a head drive slot 36 of bristle head 18 resulting in an oscillatory rotating motion imparted to bristle head 18 by coupling engagement with pivot arm 30.

FIG. 4b shows respective orientations of the apparatus of the bristle head assembly in another rotation orientation of drive shaft 24. Further rotation of drive shaft 24 from the orientation of FIG. 4a to the orientation of FIG. 4b causes the drive shaft offset end 28 to rotate pivot arm 30 into an axially parallel relationship between pivot arm 30 and drive shaft 24. From the drive shaft rotation orientation of FIG. 4b, further rotation of drive shaft 24 will result in the respective orientations of the apparatus of the bristle head assembly to be arranged as depicted in FIG. 4c. In the orientation of FIG. 4c, the drive shaft offset end 28 rotates pivot arm 30 in the counter-clockwise direction from the position of FIG. 4b to the most counter-clockwise point of rotation as depicted in FIG. 4c. Continued rotation of drive shaft 24 will cause the drive shaft offset end 28 to return to the substantially parallel relationship of FIG. 4b. In this manner, rotation of drive shaft 24 causes bristle head 18 to rotate about head pin 38 in an oscillatory fashion. The direction of rotation of the drive shaft 24 is immaterial to the manner of operation of the invention. While the foregoing description with reference to the rotation of the drive shaft 24 has been in sequence from FIGS. 4a, 4b and 4c, it will be understood that the opposite rotational direction is equally applicable. That is, a reverse rotational direction of drive shaft 24 to sequence the bristle head assembly apparatus through FIGS. 4c, 4b and 4a will also effect oscillatory rotation of bristle head 18 with respect to bristle head assembly 16.

To facilitate oscillation of bristle head 18 consequent on pivoting movement of pivot arm 30, head drive slot 36 is dimensioned to correspond substantially to the width of drive pin 34 in one cross sectional dimension, namely, in the dimension circumferential to said bristle head. In the orthogonal cross sectional dimension, namely the dimension radial to said bristle head, head drive slot 36 has a length sufficient to accommodate radial displacement of drive pin 34 consequent on the movement of bristle head 18 through the operating range of oscillation. The operating range of oscillation is depicted in FIGS. 4a, 4b and 4c.

FIGS. 5a and 5b show the moving elements of the preferred embodiment of the invention and FIG. 6 shows a side cross-section view of the bristle head assembly taken along cutting line 6—6 of FIG. 2.

FIG. 7 is a side elevation view of the pivot arm shown generally by reference numeral 30. Drive shaft 24 is coupled to an end of pivot arm 30. Coupling of drive shaft 24 to pivot arm 30 is preferably effected by providing a pivot drive slot 40 in pivot arm 30 dimensioned to receive a drive shaft engagement element 44 extending from the offset end 28. Pivot drive slot 40 has a width substantially corresponding to the width of drive shaft engagement element 44 and has an upper and lower extremity 42 defining a length to accommodate the vertical travel of the engagement element 44 during rotation of drive shaft 24. The engaging element 44 may extend parallel to the axis of drive shaft 24 or may be angled. If engagement element 44 is angled, it is preferably angled to correspond with the angular displacement of pivot arm 30 at the outermost clockwise or counter-clockwise angular displacement of the pivot arm about pivot axis 32. The angular displacement of the arm 30 about pivot axis 32 is shown in FIGS. 4a and 4c. If the engagement element 44 is angled, upper and lower extremities 42 of slot 40 may also be provided with a correspondingly angled inclination to that of the engagement element 44.

As shown most clearly in FIG. 7, the relative lengths A and B, of the drive end 46 and driven end 48 respectively of the pivot arm 30 may be varied. The relative lengths of the drive end and driven end of pivot arm 30 control the oscillation range of angular displacement of bristle head 18. In the preferred configuration, length B is greater than length A. In the configuration of the preferred embodiment, the lever action of pivot arm 30 enables the limited range of angular displacement that offset 28 is capable of imparting to drive end 46 of pivot arm 30 to be translated into a larger range of angular displacement that driven end 48 is capable of imparting to bristle head 18. In this arrangement, oscillating angular displacement of bristle head 18 to include rotations efficacious for cleaning teeth or oral surfaces with pliable bristles, including various pliabilities such as soft, medium or hard bristles, can be readily obtained.

Figure 8:
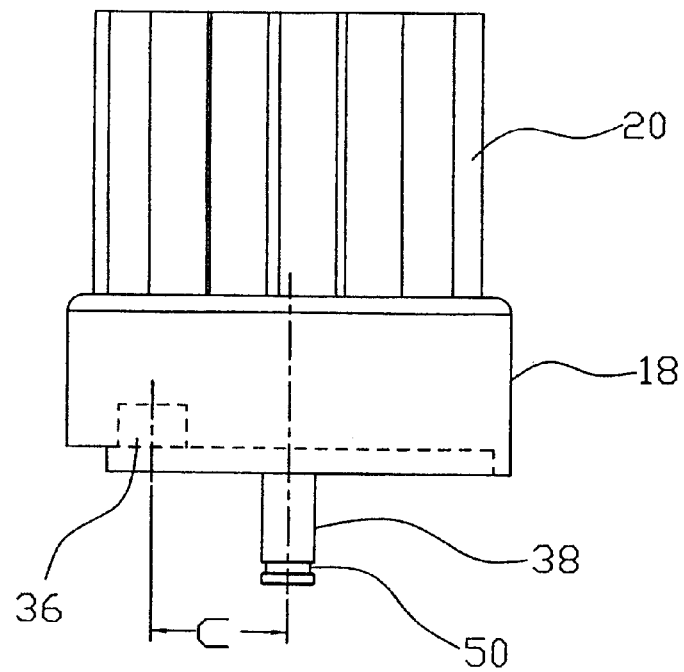
FIG. 8 is an elevation view of a bristle head.

FIG. 8 shows a side elevational view of a preferred embodiment of the bristle head 18. The bristle head 18 has a head pin 38 for rotating engagement with a corresponding mating hole 39 (see FIG. 6) of the bristle head assembly 16. Securing means, preferably in the form of a groove 50 and corresponding mating engaging seat 52 provided in the mating hole 39 of the bristle head assembly 16, retaining the bristle head 18 on the bristle head assembly. Head slot 48 is provided at a radial distance C from the head pin 38 as required to obtain optimal rotational displacement of bristle head 18 about head pin 38 during operation of the tooth brush. The radial distance C is located to facilitate an optimal torque to be applied to the bristle head 18 by the prime mover of the electric toothbrush to effect efficacious cleaning in the oscillation of the bristle head 18. Increasing the radial distance C that head slot 40 is from head pin 38 will increase the torque that can be applied to bristle head 18 for a given power output of the toothbrush prime mover but with consequent decrease in rotational displacement of bristle head 18. Conversely, decreasing the radial displacement distance C that head slot 40 is from head pin 38 will decrease the torque applied to bristle head 18 for a given power output of the toothbrush prime mover but with a consequent increase in the angular displacement of the bristle head 18.

Now that the invention has been described with reference to the preferred embodiments disclosed here and in the drawings, numerous substitutions and mechanical equivalents will occur to those skilled in the art. The invention is not limited to the exact structure and embodiments depicted herein, but rather is defined in the claims appended hereto.

I claim:

1. A bristle head oscillation mechanism for an electrically driven toothbrush comprising:
   (i) an elongate housing having a drive shaft rotatably mounted therein;
   (ii) a bristle head rotatably disposed at an end of said elongate housing and
   (iii) a pivot arm pivotable about a pivot axis depending from said housing, one end of said pivot arm forming a drive slot coupled to an off set end of said drive shaft thereby coupling said pivot arm to said drive shaft and a coupling on an opposing end of said pivot arm adapted to engage said bristle head, said coupling including a drive pin and a mating drive slot, wherein said pivot arm has a first length characterising the distance between the pivot arm coupling to said bristle head and said pivot axis and a second length characterising the distance between the pivot arm coupling to said drive shaft and said pivot axis such that the first length is greater than the second length whereby rotation of said drive shaft pivots said pivot arm to effect oscillation of said bristle head in relation to said elongate housing.

2. The apparatus as claimed in claim 1 wherein said oscillation of said bristle head is not less than forty degrees of rotation.

3. The apparatus of claim 1 further including mounting means extending from an end of said elongate housing opposed to said bristle head, the mounting means adapted to releasably couple to a powered handle of an electrically driven toothbrush whereby said elongate housing becomes mechanically interconnected with said powered handle and said drive shaft is adapted to be driven in rotation thereby.

4. The apparatus of claim 1 wherein said bristle head is disposed to provide an axis of rotation that is substantially orthogonal to the longer dimension of said elongate housing.

5. The apparatus of claim 1 wherein said drive pin of said coupling extends from said pivot arm and said mating drive slot is formed in said bristle head.

6. A bristle head oscillation mechanism for an electrically driven toothbrush comprising:
   (i) an elongate housing having a drive shaft rotatably mounted therein;
   (ii) a bristle head rotatably disposed at an end of said elongate housing and
   (iii) a pivot arm pivotable about a pivot axis depending from said housing, one end of said pivot arm forming a drive slot coupled to an off set end of said drive shaft thereby coupling said pivot.arm to said drive shaft and a drive pin extending from an opposing end of said pivot arm to engage a mating drive slot formed in said bristle head to couple said pivot arm to said bristle head, wherein said pivot arm has a first length characterising the distance between the pivot arm coupling to said bristle head and said pivot axis and a second length characterising the distance between the pivot arm coupling to said drive shaft and said pivot axis such that the first length is greater than the second length whereby rotation of said drive shaft pivots said pivot arm to effect oscillation of said bristle head in relation to said elongate housing.

7. The apparatus as claimed in claim 6 wherein said oscillation of said bristle head is not less than forty degrees of rotation.

8. The apparatus of claim 6 further including mounting means extending from an end of said elongate housing opposed to said bristle head, the mounting means adapted to releasably couple to a powered handle of an electrically driven toothbrush whereby said elongate housing becomes mechanically interconnected with said powered handle and said drive shaft is adapted to be driven in rotation thereby.

9. The apparatus of claim 6 wherein-said bristle head is disposed to provide an axis of rotation that is substantially orthogonal to the longer dimension of said elongate housing.

10. A bristle head oscillation mechanism for an electrically driven toothbrush comprising:
   (i) an elongate housing having a drive shaft rotatably mounted therein;
   (ii) a bristle head rotatably disposed about a bristle head axis at an end of said elongate housing and
   (iii) a pivot arm pivotable about a pivot axis depending from said housing, one end of said pivot arm forming a drive slot coupled to an off set end of said drive shaft thereby coupling said pivot arm to said drive shaft and a coupling on an opposing end of said pivot arm adapted to engage said bristle head between said bristle head axis and said pivot axis, said coupling including a drive pin slideably engaging a mating drive slot, whereby rotation of said drive shaft pivots said pivot arm to effect oscillation of said bristle head in relation to said elongate housing.

11. The apparatus as claimed in claim 10 wherein said pivot arm has a first length characterising the distance between the pivot arm coupling to said bristle head and said pivot axis and a second length characterising the distance between the pivot arm coupling to said drive shaft and said pivot axis such that the first length is greater than the second length.

12. The apparatus as claimed in claim 11 wherein said oscillation of said bristle head is not less than forty degrees of rotation.

13. The apparatus of claim 11 wherein said bristle head is disposed to provide an axis of rotation that is substantially orthogonal to the longer dimension of said elongate housing.

14. The apparatus as claimed in claim 10 wherein said oscillation of said bristle head is not less than forty degrees of rotation.

15. The apparatus of claim 10 further including mounting means extending from an end of said elongate housing opposed to said bristle head, the mounting means adapted to releasably couple to a powered handle of an electrically driven toothbrush whereby said elongate housing becomes mechanically interconnected with said powered handle and said drive shaft is adapted to be driven in rotation thereby.

16. The apparatus of claim 10 wherein said bristle head is disposed to provide an axis of rotation that is substantially orthogonal to the longer dimension of said elongate housing.

17. The apparatus of claim 10 wherein said drive pin of said coupling extends from said pivot arm and said mating drive slot is formed in said bristle head.

18. A bristle head oscillation mechanism for an electrically driven toothbrush comprising:
   (i) an elongate housing having a drive shaft rotatably mounted therein;
   (ii) a bristle head rotatably disposed about a bristle head axis at an end of said elongate housing and
   (iii) a pivot arm pivotable about a pivot axis depending from said housing, one end of said pivot arm forming a drive slot coupled to an off set end of said drive shaft thereby coupling said pivot arm to said drive shaft and a drive pin extending from an opposing end of said pivot arm to slideably engage a mating drive slot formed in said bristle head between said bristle head axis and said pivot axis at a selected distance from said bristle head axis to couple said pivot arm to said bristle head, whereby rotation of said drive shaft pivots said pivot arm to effect oscillation of said bristle head in relation to said elongate housing facilitating an optimal torque to be applied to said bristle head.

19. The apparatus as claimed in claim 18 wherein said pivot arm has a first length characterising the distance between the pivot arm coupling to said bristle head and said pivot axis and a second length characterising the distance between the pivot arm coupling to said drive shaft and said pivot axis such that the first length is greater than the second length.

20. The apparatus as claimed in claim 19 wherein said oscillation of said bristle head is not less than forty degrees of rotation.

21. The apparatus of claim 19 wherein said bristle head is disposed to provide an axis of rotation that is substantially orthogonal to the longer dimension of said elongate housing.

22. The apparatus as chimed in claim 18 wherein said oscillation of said bristle head is not less than forty degrees of rotation.

23. The apparatus of claim 18 further including mounting means extending from an end of said elongate housing opposed to said bristle head, the mounting means adapted to releasably couple to a powered handle of an electrically driven toothbrush whereby said elongate housing becomes mechanically interconnected with said powered handle and said drive shaft is adapted to be driven in rotation thereby.

24. The apparatus of claim 18 wherein said bristle head is disposed to provide an axis of rotation that is substantially orthogonal to the longer dimension of said elongate housing.

* * * * *